(12) United States Patent
Hecker et al.

(10) Patent No.: US 8,556,800 B2
(45) Date of Patent: Oct. 15, 2013

(54) LUBRICANT SUPPLYING DEVICE FOR THE EVERTING TUBE DRIVE OF AN ENDOSCOPE

(75) Inventors: Albert Hecker, Mering (DE); Guenter Wilhelm Schuetz, Meitingen (DE); Wilhelm Franz Pommersheim, Adelsried (DE)

(73) Assignee: Invendo Medical GmbH, Kissing (DE)

( * ) Notice: Subject to any disclaimer, the term of this patent is extended or adjusted under 35 U.S.C. 154(b) by 257 days.

(21) Appl. No.: 12/942,767

(22) Filed: Nov. 9, 2010

(65) Prior Publication Data

US 2011/0137119 A1 Jun. 9, 2011

(30) Foreign Application Priority Data

Nov. 9, 2009 (DE) .......................... 10 2009 052 386

(51) Int. Cl.
*A61B 1/00* (2006.01)

(52) U.S. Cl.
USPC ............ 600/114; 600/104; 600/106; 604/271

(58) Field of Classification Search
USPC ......... 600/104, 106, 114–116, 101, 139–152; 604/264–271; 606/1, 108
See application file for complete search history.

(56) References Cited

U.S. PATENT DOCUMENTS

| 3,669,099 | A | * | 6/1972 | Silverman | 600/581 |
|---|---|---|---|---|---|
| 4,321,915 | A | * | 3/1982 | Leighton et al. | 600/114 |
| 5,045,070 | A | * | 9/1991 | Grodecki et al. | 604/271 |
| 5,236,423 | A | * | 8/1993 | Mix et al. | 604/271 |
| 5,586,968 | A | * | 12/1996 | Grundl et al. | 600/114 |
| 6,077,219 | A | * | 6/2000 | Viebach et al. | 600/114 |
| 6,358,199 | B1 | * | 3/2002 | Pauker et al. | 600/114 |
| 6,554,793 | B1 | * | 4/2003 | Pauker et al. | 604/95.01 |
| 6,971,990 | B2 | * | 12/2005 | Ziegler et al. | 600/114 |
| 7,172,552 | B2 | * | 2/2007 | Wendlandt | 600/114 |
| 7,708,687 | B2 | * | 5/2010 | Bern et al. | 600/115 |
| 2006/0020164 | A1 | * | 1/2006 | Butler et al. | 600/115 |
| 2006/0264707 | A1 | * | 11/2006 | Kinney | 600/115 |
| 2008/0058596 | A1 | * | 3/2008 | Bob et al. | 600/114 |

* cited by examiner

*Primary Examiner* — Matthew J Kasztejna
*Assistant Examiner* — Ryan Henderson
(74) *Attorney, Agent, or Firm* — AlbertDhand LLP

(57) ABSTRACT

A lubricant supplying device of an endoscope everting tube drive comprises a drive tube everted at least once to thus form an outer and an inner tube portion. Inside the inner tube portion an endoscope shaft is mounted in an axially displaceable manner. In addition a drive device is provided which encompasses the drive tube everted at least once or the inner tube portion thereof so as to apply a driving force for an advancing movement of the endoscope shaft onto the inner tube portion, the drive means being in fluid connection with a lubricant supplying line and a lubricant discharge line for introducing a lubricant via the drive device into the drive tube everted at least once and/or for discharging it. The lubricant supply line and the lubricant discharge are connected to the drive device in two locations thereof diametrically opposite with respect to the endoscope shaft.

6 Claims, 1 Drawing Sheet

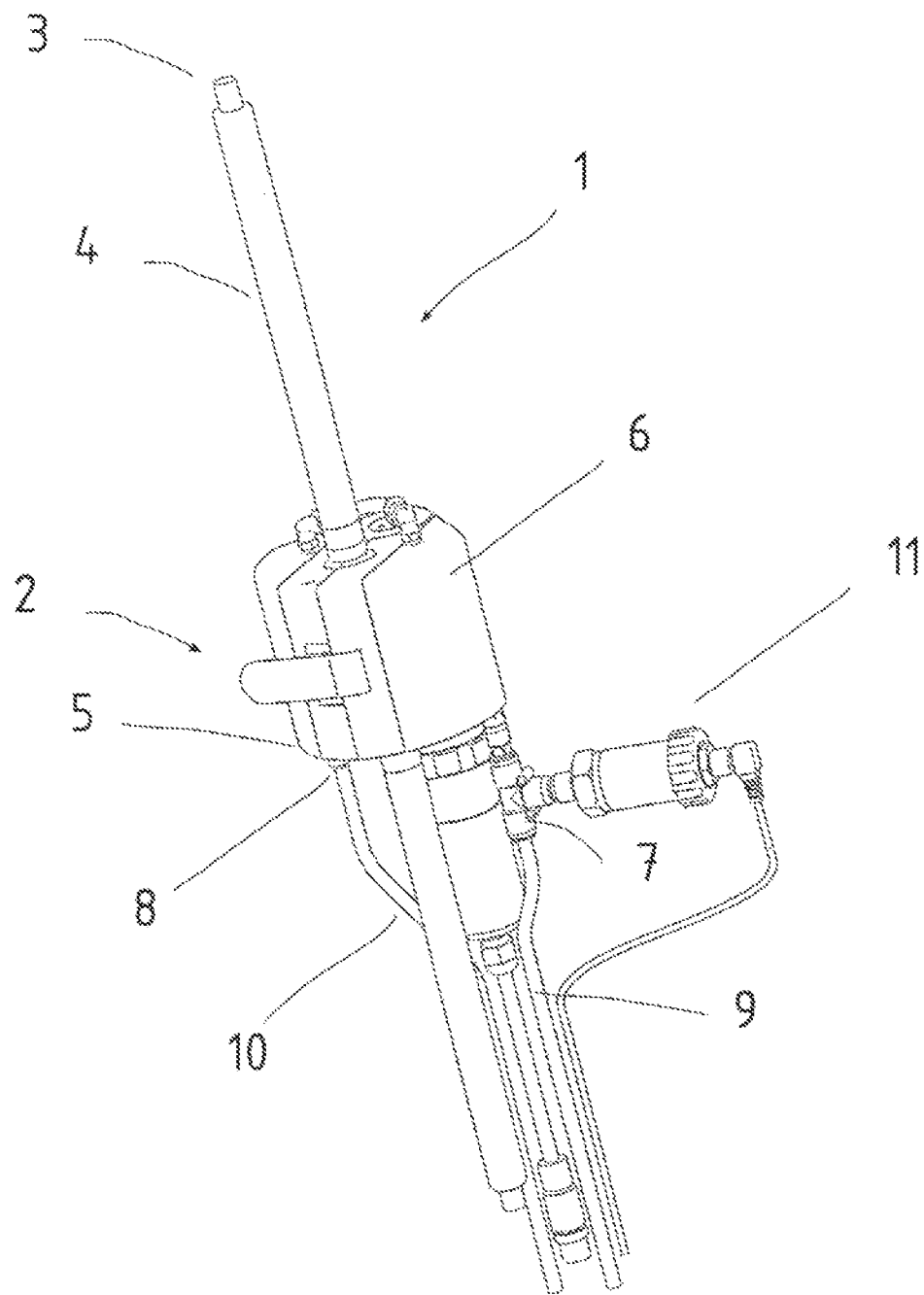

LUBRICANT SUPPLYING DEVICE FOR THE EVERTING TUBE DRIVE OF AN ENDOSCOPE

The present invention relates to a lubricant supplying device for the everting tube drive of an endoscope.

Recently, endoscopes are being introduced over considerable distances (as far as 2.5 m) into a patient's colon for an examination of the latter as to pathological changes in tissue (such as cancer), and in a given case for treatment. In order to overcome this long insertion distance, novel endoscopes are equipped with drive devices consisting, for example, of an everting tube surrounding the endoscope shaft, which may be moved forward by means of a drive device to thereby exert an advancing force on the endoscope shaft.

From the prior art, in particular from the prior art by the applicant of the present invention, a like everting tube drive for forward and reverse driving of an endoscope shaft has become known through a multiplicity of patent publications. The known everting tube drive consists of a tube everted, or reversed, at a distal and a proximal end (twice-everted tube) having a drive device arranged in its central portion. The respective everted ends of the tube are returned to this drive device and preferably immobilized at the casing of the drive device.

The drive device proper is either made up of a continuous advancing mechanism preferably comprised of a number of drive wheels or a conveyor, or of a non-continuous drive mechanism. The drive device basically only drives the everting tube which in turn applies a driving force to the endoscope shaft. In such a case it is required in terms of kinematics for the endoscope shaft to slide relative to the everting tube so as prevent the endoscope shaft from moving ahead of the distal everted end of the everting tube. Particularly at the desired penetration depths of the endoscope, however, considerable frictional forces are generated between the endoscope shaft and the everting tube as well as within the everting tube, which may cause the advancing movement of the endoscope to come to a halt after a certain penetration depth.

For this reason the pressurized introduction of lubricants into cavities between two surfaces executing a relative sliding movement had already been known from the prior art, to thereby minimize frictional forces. As a patient's colon does not extend linearly, however, but exhibits a multiplicity of curvatures, the endoscope is bound to follow these curvatures, wherein—particularly in curvature areas—the surfaces of tube and shaft elements sliding relative to each other enter into direct contact with each other and thus squeeze lubricant from these areas. Based on a multiplicity of experiments the applicant came to notice that this phenomenon of lubricant partially being squeezed out is aggravated by air pockets which are introduced while the endoscope is being filled with lubricant.

In view of this set of problems, the present invention is based on the object of providing a lubricant supplying device for the everting tube drive of an endoscope of the above-mentioned type, whereby it is possible to obtain a substantially continuous lubricating film over the entire endoscope length.

This object is achieved through a lubricant supplying device having the features of the claims. Advantageous aspects of the invention are subject matter of the subclaims.

The basic concept of the invention consists in providing a lubricant supplying device of an endoscope everting tube drive including a drive tube which is reversed at least once so as to form an outer and an inner tube portion. Inside the inner tube portion, an endoscope shaft is mounted for axial displacement. Moreover a drive device is provided which encompasses the drive tube everted at least once, or the inner tube portion thereof, so as to apply a driving force for an advancing movement of the endoscope shaft onto the inner tube portion. The drive device is in fluid connection with a lubricant supply line and a lubricant discharge line, whereby a lubricant may be introduced into and/or discharged from the drive means in the drive tube everted at least once. The lubricant supply line and the lubricant discharge line are arranged in two locations of the drive means that are diametrically opposite with respect to the endoscope shaft.

Depending on whether the everting tube—i.e., the annular gap between the inner and outer tube portions—is to be filled with lubricant or lubricant is to be disposed of, this constructive design allows to utilize the supply line or the discharge line as a ventilating or exhausting line. Specifically, the diametrical disposition of supply and discharge lines with respect to the endoscope shaft allows the latter to be rotated about its longitudinal axis so as to selectively position the two lines upwardly of the shaft relative to gravity. During filling, the port for the discharge line accordingly is arranged upwardly of the shaft, so that air displaced during filling with lubricant may be exhausted entirely via the discharge line. In the case of disposal, the port for the supply line is arranged upwardly of the shaft, so that air may be replenished from the annular gap while lubricant is being discharged.

Advantageously, a position sensor is disposed at the drive device, in particular in or on the casing of the drive device, for detecting the rotational position of the casing and thus the relative position with regard to gravity of the two lines leading to the endoscope shaft, and for reporting to a control means. The control means is preferably configured to start or admit the filling or discharging operation only if the relative positions in accordance with the above definition are detected or confirmed by the sensor.

It is furthermore advantageous if the lubricant lines of the endoscope of the invention are laid in parallel with the endoscope shaft and are preferably connected to an axial end face of the drive casing. In this way it is possible to avoid or reduce an inclusion of air in the lines, so that an additional introduction of air via the lines is prevented particularly during filling of the tube drive.

The invention shall in the following be explained in more detail by way of a preferred embodiment while making reference to the single figure.

The single figure shows a schematic representation of a lubricant supplying device of an everting tube drive for an endoscope in accordance with a preferred embodiment of the invention.

The figure shows the central portion of an endoscope 1 in the area of the endoscope drive. Accordingly, the endoscope 1 of the invention consists of an endoscope shaft 3 sheathed by an everting tube 4. In the present case, the everting tube 4 is a so-called twice-everted tube which is reversed at a distal end and at a proximal end of the endoscope shaft 3. As an alternative, however, the everting tube 4 may consist of a once-everted tube having a reversing portion at the distal end of the endoscope shaft 3 only. The present twice-everted tube accordingly forms an inner tube portion in direct contact with the endoscope shaft 3, as well as two outer tube portions which are formed by the eversions at the proximal and distal ends of the endoscope shaft 3 and which are led back to a drive device 5. The ends of the outer tube portions are immobilized on a casing 6 of the drive device 5.

Inside the casing 6 of the drive device 5, a drive means is mounted, for instance a number of drive wheels or the like advancing mechanisms which are operated electrically, hydraulically or pneumatically. Here the drive device 5 exerts a driving force on the inner tube portion of the twice-everted tube 4 so as to displace the latter along the endoscope shaft 3. This advancing movement of the twice-everted tube 4 is transmitted to endoscope shaft 3 at a distal and a proximal stop part thereof, with the endoscope shaft 3 thus being dragged along in the respective advancing direction.

In order to enhance slidability between the inner tube portion and the endoscope shaft 3, as well as between the inner tube portion and the respective outer tube portions, lubricants are introduced under a certain pressure into the gap-type cavities between the tube portions and the endoscope shaft.

To this end, in the present embodiment the drive casing 6 is provided with two ports 7, 8 having a substantially diametrically opposed position with regard to the endoscope shaft 3. One port 7 serves for filling the drive device 5 with lubricant, while the other port 8 serves for evacuating the lubricant from the drive device 5. For this purpose a lubricant supply line 9 is connected to the filling port 7, and an evacuation line 10 to the discharge port 8. This allows the pressurized introduction of lubricant via the filling port 7 into the inside of the casing, from where it is passed on via openings having the drive means such as, e.g., drive wheels mounted in them, into a gap between the inner tube portion and the outer tube portions. Here it is necessary to avoid in the highest possible degree the introduction of air bubbles during the filling operation, so as to allow the lubricating film forming inside the everting tube 4 to be preserved substantially over the entire length of the everting tube. In addition, lubricant already present inside the drive must be emptied as completely as possible after the end of an examination so as to avoid a possible contamination of the drive by organic material originating from the patient.

The diametrical arrangement of filling port 7 and evacuation port 8 with regard to the endoscope shaft 3 allows, by making use of gravity, to fill the everting tube 4 in such a way that air contained in the everting tube drive may leave via the evacuation port 8. On the other hand, the everting tube drive may be emptied of used lubricant without lubricant residues being left behind in the drive.

Specifically, this is achieved by rotating the everting tube drive for the filling operation in such a way that the filling port 7 is situated below and the evacuation port 8 is situated above with regard to the endoscope shaft 3. If, in this three-dimensional position, lubricant is pumped via the filling line 9 into the casing 6 of the drive device 5, the air inside the everting tube 4 and the drive casing 6 may exit completely via the opposed evacuation port 8 having an opposite position, i.e., situated above. For the evacuating operation the everting tube drive is rotated about 180 degrees, so that the filling port 9 is placed above with respect to the endoscope shaft 3 and the evacuation port 8 assumes a position below the endoscope shaft. In this three-dimensional position, the lubricant may now be evacuated completely from the everting tube drive, with the filling port 7 serving as an air replenishing opening in this case.

It was found in practice that a correct execution of the filling and evacuating operations is in the user's responsibility and thus constitutes a source of errors that may not be neglected. In other words, incorrect filling of the system virtually inevitably results in air pockets which are only noticed during the treatment phase when the endoscope has already been inserted. In order to preclude this source of errors, a position sensor 11, for example a (3-axis) acceleration sensor, is integrated to the casing 6 of the drive device 5 or externally flanged to the casing 6. The position sensor 11 emits signals to an external control means (not represented) which accordingly is capable of determining the position of the casing 6 relative to gravity.

The control means is programmed to start or admit a filling operation or an evacuating operation only if the evaluation of the sensor signals indicates the drive 5 or the drive casing 6 to be in its appropriate position as described in the foregoing. In this way it is possible to avoid faulty filling or incomplete disposal of used lubricant.

The invention claimed is:

1. A lubricant supplying device of an endoscope everting tube drive comprising:
a drive tube which is everted at least once so as to form an outer and an inner tube portion and having an endoscope shaft mounted therein in an axially displaceable manner,
a drive device which encompasses at least a portion of the drive tube, the drive device configured to exert a driving force onto the inner tube portion, thereby displacing the endoscope shaft along a longitudinal axis of the endoscope shaft, the drive device further being in fluid connection with a lubricant supply line and a lubricant discharge line, the lubricant supply line being connected to the drive device at a filling port, and the lubricant discharge line being connected to the drive device at an evacuation port, the filling port and the evacuation port being arranged in an approximately diametrically opposite relationship with each other about the longitudinal axis of the endoscope shaft, and
wherein the drive device has a position sensor located so as to detect a position of each of the filling port and the evacuation port relative to the longitudinal axis of the endoscope shaft and with regard to gravity, the position sensor emitting signals relating to the positions of the filling port and the evacuation port.

2. The lubricant supplying device according to claim 1, further comprising a control means connected to the position sensor, the control means determining, based on signals emitted by the position sensor, the respective location of the filling port with regard to gravity and at least one of the longitudinal axis of the endoscope shaft or the evacuation port.

3. The lubricant supplying device according to claim 2, wherein the control means starts or admits a lubricant supplying process only if the filling port is situated below the endoscope shaft.

4. The lubricant supplying device according to claim 3, wherein the control means starts or admits a lubricant discharging process only if the evacuation port is situated below the endoscope shaft.

5. The lubricant supplying device according to claim 1, the drive device having a casing which encompasses the inner tube portion of the drive tube and to which the lubricant supply line and the lubricant discharge line are connected, at an axial end face of the casing with regard to the endoscope shaft.

6. An endoscope comprising:
an endoscope shaft,
an everting tube drive, the everting tube drive further comprising:
a drive tube which is everted twice, so as to form an outer and an inner tube portion and having an endoscope shaft mounted therein in an axially displaceable manner,
a drive device which encompasses at least a portion of the drive tube, the drive device configured to exert a driving force onto the inner tube portion, thereby displacing the endoscope shaft along a longitudinal axis of the endoscope shaft, the drive device further being in fluid connection with a lubricant supply line and a lubricant discharge line, the lubricant supply line being connected to the drive device at a filling port, and the lubricant discharge line being connected to the drive device at an evacuation port, the filling port and the evacuation port being arranged in an approximately diametrically opposite relationship with each other about the longitudinal axis of the endoscope shaft, and wherein the drive device has a position sensor located so as to detect a position of each of the filling port and the evacuation port relative to the longitudinal axis of the endoscope shaft and with regard to gravity, the position sensor emitting signals relating to the positions of the filling port and the evacuation port.

\* \* \* \* \*